(12) United States Patent
Plourde, Jr. et al.

(10) Patent No.: US 6,342,645 B2
(45) Date of Patent: Jan. 29, 2002

(54) METHODS FOR THE PRODUCTION AND ISOLATION OF D-CHIRO-INOSITOL FROM KASUGAMYCIN AND THE USE OF D-CHIRO-INOSITOL OBTAINED THEREFROM

(75) Inventors: Robert Plourde, Jr., Richmond; Mark C. Sleevi, Midlothian; Rachel K. Longo, Mechanicsville, all of VA (US)

(73) Assignee: Insmed Pharmaceuticals, Inc., Richmond, VA (US)

( * ) Notice: Subject to any disclaimer, the term of this patent is extended or adjusted under 35 U.S.C. 154(b) by 0 days.

(21) Appl. No.: 09/750,193

(22) Filed: Dec. 29, 2000

Related U.S. Application Data (60) Provisional application No. 60/173,554, filed on Dec. 30, 1999.

(51) Int. Cl.[7] ........................... C07C 35/14; C07C 35/08
(52) U.S. Cl. ....................................... 568/833; 568/832
(58) Field of Search .................................. 568/833, 832

(56) References Cited

U.S. PATENT DOCUMENTS 5,091,596 A  *  2/1992  Kennington et al. ......... 568/833
5,714,643 A  *  2/1998  Sato et al. .................. 568/833

* cited by examiner

*Primary Examiner*—Johann Richter
*Assistant Examiner*—Elvis O. Price
(74) *Attorney, Agent, or Firm*—Sterne, Kessler, Goldstein & Fox PLLC (57) ABSTRACT

The present invention relates to methods for the production and isolation of D-chiro-inositol (DCI) from kasugamycin. More specifically, the present invention relates to a method of producing DCI by hydrolysis of kasugamycin with aqueous trifluoroacetic acid in the presence of a strongly acidic ion exchange resin. The present invention further relates to methods of isolating DCI from an aqueous mixture, such as a hydrolysis mixture, either directly or by forming an organic derivative of DCI.

2 Claims, 1 Drawing Sheet

Figure 1

METHODS FOR THE PRODUCTION AND ISOLATION OF D-CHIRO-INOSITOL FROM KASUGAMYCIN AND THE USE OF D-CHIRO-INOSITOL OBTAINED THEREFROM

CROSS-REFERENCE TO RELATED APPLICATIONS

This application claims priority to U.S. Provisional Application No. 60/173,554, filed Dec. 30, 1999, which is herein incorporated by reference.

STATEMENT REGARDING FEDERALLY-SPONSORED RESEARCH AND DEVELOPMENT

Not applicable.

REFERENCE TO MICROFICHE APPENDIX/SEQUENCE LISTING/TABLE/COMPUTER PROGRAM LISTING APPENDIX Submitted on a Compact Disc and an Incorporation-by-reference of the Material on the Compact Disc Not applicable.

BACKGROUND OF THE INVENTION

D-chiro-inositol (DCI) is a rare isomer of inositol that, in recent years, has been implicated as having, a role in the activity of insulin on the body. Recent clinical trials have brought forth its potential pharmacological value for the treatment of diseases of insulin resistance.

For example, in a recent Phase II clinical study with 44 women afflicted with polycystic ovary syndrome (PCOS), administration of DCI (1200 mg/day for 6–8 weeks) resulted in ovulation by 86% of the patients, contrasted to ovulation in only 27% of the control (placebo) subjects (Nestler et al., N. Engl. J. Med. 340:1314–1320 (1999)). Similarly, in a clinical study of subjects with impaired glucose tolerance, administration of DCI (1200 mg/day for 2 weeks) restored glucose tolerance and insulin secretion to normal levels (Kessler et al., Diabetes Abst. 58th Scientific Sessions, #1385, A358 (1998)).

Figure 1:
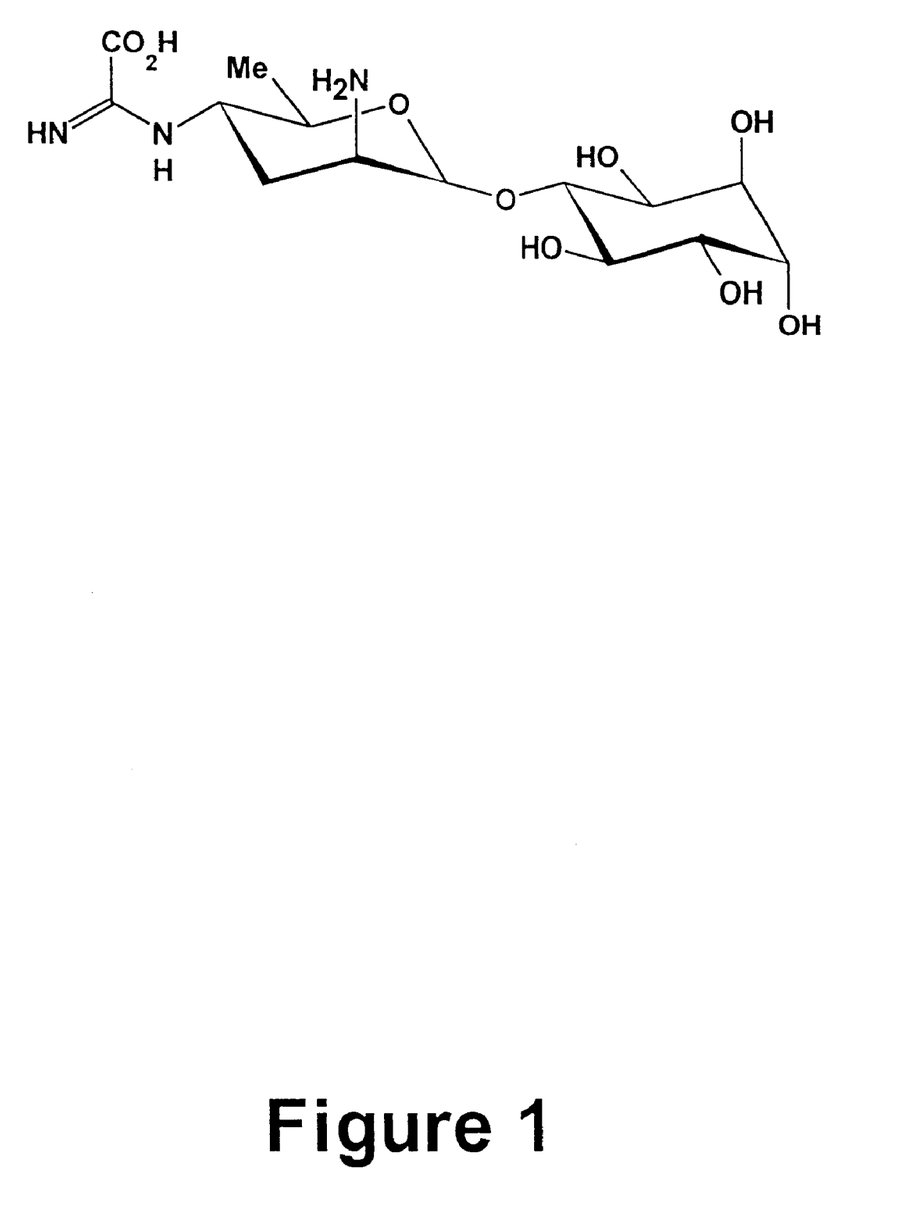
FIG. 1. Structure of kasugamycin.

An excellent source of DCI is the aminoglycoside kasugamycin, a fermentation product of Streptomyces kasugaspinus and Streptomyces kasugaensis, which contains a molecule of DCI bound through a glycosidic linkage to the aminosugar kasugamine. Treatment of kasugamycin with strong acid cleaves this glycosidic linkage, liberating DCI and kasugamine, along with various other nitrogen-containing side products (FIG. 1).

The methods currently used to hydrolyze kasugamycin and liberate DCI require large volumes of strongly acidic aqueous solutions (Kennington et al., U.S. Pat. No. 5,091,596) or large quantities of strongly acidic ion exchange resin (Sato et al., U.S. Pat. No. 5,714,643). In addition, prolonged reaction times and high temperatures and/or high pressures are required to complete the hydrolysis.

Moreover, for the production of meaningful quantities of DCI, these methods require the use of large volumes of high-boiling aqueous solutions. Purification of DCI from such a hydrolysis mixture requires processing through similarly large volumes of expensive anionic and cationic ion exchange resins, much of which are spent neutralizing the acids.

An alternative method for the production of DCI from kasugamycin is acetolysis. An advantage of this process is that it eliminates the need for ion exchange chromatography. Disadvantages, however, include the difficulties in removing the acetylating reagent and the production of side products. Extensive processing of the reaction mixture is generally required to remove these side products and so isolate pure DCI. (Riley et al., U.S. Pat. Nos. 5,463,142; 5,932,774).

In view of its high therapeutic potential and the ongoing studies involving treatment with DCI, there remains a need in the art for simple and efficient methods of preparing and/or isolating pure DCI without any of the disadvantages of present methods.

FIELD OF THE INVENTION

The present invention relates to methods for the production and isolation of D-chiro-inositol (DCI) from kasugamycin. More specifically, the present invention relates to a method of producing DCI by hydrolysis of kasugamycin with aqueous tritluoroacetic acid in the presence of a strongly acidic ion exchange resin. The present invention further relates to methods of isolating DCI from an aqueous mixture such as a hydrolysis mixture, either directly or by forming an organic derivative of DCI.

BACKGROUND ART

Not applicable.

BRIEF SUMMARY OF THE INVENTION

Accordingly, a first embodiment of the present invention relates to a method for producing DCI from kasugamycin, which comprises hydrolyzing kasugamycin in an aqueous solution of trifluoroacetic acid (TFA) in the presence of a strongly acidic ion exchange resin and then isolating DCI from the product mixture.

A second embodiment of the present invention relates to a method for solating DCI from a product mixture resulting from an acid hydrolysis of kasugamycin, which comprises contacting an aqueous solution of the reaction mixture sequentially with: (i) a not more than 12-fold excess of a basic (or ionic) ion exchange resin; and (ii) a not more than 6-fold excess of an acidic or cationic) ion exchange resin.

A third embodiment of the present invention relates to a second method for isolating DCI from a product mixture resulting from an acid hydrolysis of kasugamycin, which comprises preparing, an organic derivative of DCI and then isolating the derivatized DCI using an organic solvent extraction.

A fourth embodiment of the present invention relates to the pharmaceutical uses of DCI prepared and/or isolated according to any of the methods of the present invention.

DETAILED DESCRIPTION OF THE INVENTION

The present invention relates to methods for the production and isolation of D-chiro-inositol (DCI) from kasugamycin. More specifically, the present invention relates to a method of producing DCI by hydrolysis of kasugamycin with aqueous trifluoroacetic acid in the presence of a strongly acidic ion exchange resin. The present invention further relates to methods of isolating DCI from an aqueous mixture, such as a hydrolysis mixture, either directly or through the formation of an organic derivative of DCI.

I. Hydrolysis of Kasugamycin

A first preferred embodiment of the present invention is directed to a method for producing DCI from kasugamycin, which comprises hydrolyzing kasugamycin in an aqueous solution of trifluoroacetic acid (TFA) in the presence of a strongly acidic ion exchange resin.

Preferably, an aqueous solution of kasugamycin is combined with an aqueous solution of an effective amount of trifluoroacetic acid (TFA) and an effective amount of strongly acidic ion exchange resin to form a reaction mixture. This reaction mixture is maintained for a time sufficient for the kasugamycin to be hydrolyzed to DCI, kasugamine and other by-products. Preferably, this reaction mixture is maintained for a time sufficient for all of the kasugamycin to be hydrolyzed.

The aqueous solution of TFA preferably contains no more than about 20% water, more preferably no more than about 15% water, and most preferably no more than about 10% water. A particularly preferred aqueous solution of TFA contains between about 2% and about 20% water, more preferably between about 2% and about 15% water, and most preferably between about 2% and about 10% water. Suitable aqueous solutions of TFA may be obtained from any of the known commercial sources (e.g. Sigma-Aldrich, Lancaster, ICN or the like) or, in the alternative, may be prepared by adding an appropriate amount of TFA or a suitable TFA precursor, such as trifluoroacetic anhydride, to a sufficient quantity of water.

The amount of aqueous solution of TFA employed in this embodiment of the present invention is that amount which is effective for the hydrolysis of a predetermined amount of kasugamycin to a desired amount of DCI. Such amounts may be determined empirically by one skilled in the art considering such factors as, for example, the concentration of the aqueous solution of TFA and the amount of cationic ion exchange resin present in the reaction mixture.

The concentration of kasugamycin in the reaction mixture is preferably between about 5% and about 40%, more preferably between about 10% and about 30%.

The acidic ion-exchange resin is preferably a strongly acidic ion-exchange resin. Suitable resins which may be employed in this embodiment of the present invention are any of the acidic ion-exchange resins known and available to those skilled in the art. Preferably, the acidic ion-exchange resin is a polystyrene-based sulfonic acid resin. Suitable examples of such resins are commercially available as Amberlite®, Amberlyst®, Amberjet®, Dowex®, Dianion®, Duolite® and BioRad®.

The amount of acidic ion-exchange resin employed in the inventive method is that amount which is effective for the hydrolysis of a predetermined amount of kasugamycin to a desired amount of DCI. Such amounts may be determined empirically by one skilled in the art considering such factors as, for example, the concentration of the aqueous solution of TFA and the amount of kasugamycin. Preferably, the amount of acidic ion-exchange resin is 2–3 times (w/w) the amount of kasugamycin being hydrolyzed.

The progress of the hydrolysis may be monitored by sampling the reaction mixture and analyzing the sample using any of the methods and techniques known and available to those skilled in the art, such as thin layer chromatography, gas chromatography, gas chromatography/mass spectroscopy, HPLC and nuclear magnetic resonance spectroscopy. Preferably, the progress of the hydrolysis is monitored by sampling the reaction mixture and analyzing the sample using thin layer chromatography for such indicators as, for example, the appearance of DCI and/or the consumption of kasugamycin.

In a particularly preferred embodiment, the reaction mixture is heated to a temperature above ambient temperature (i.e. above 25° C.) for a time sufficient for the kasugamycin to be hydrolyzed. Most preferably, the reaction mixture is heated to a temperature of at least 75° C. In an especially preferred embodiment, the reaction mixture is heated to a temperature sufficient to reflux a 90–98% TFA-water mixture.

Preferably, the temperature of the reaction mixture is maintained at a temperature above ambient temperature for a time sufficient for the kasugamycin to be hydrolyzed. More preferably, the temperature of the reaction mixture is maintained at a temperature above ambient temperature for a time sufficient for all of the kasugamycin to be hydrolyzed. Even more preferably, the temperature of the reaction mixture is maintained above ambient temperature for at least 3 hours but not more than 6 hours. Most preferably, the temperature is maintained at 75° C. or reflux temperature for at least 3 hours but not more than 6 hours.

When the progress of the hydrolysis has reached the desired stage (preferably when all of the kasugamycin has been hydrolyzed), the aqueous TFA solution may be separated from the resin by filtration or decantation using any of the filtration or decantation methods and techniques known and available to those skilled in the art. The DCI may then be isolated from the aqueous TFA solution by any suitable method.

II. Isolation of DCI

A. Ion-Exchange Chromatography

A second preferred embodiment of the present invention is directed to a method for isolating DCI from a product mixture resulting from an acid hydrolysis of kasugamycin, such as the hydrolysis of kasugamycin using aqueous TFA, by sequentially contacting the product mixture first with a basic (or anionic) ion exchange resin and then with an acidic (or cationic) ion exchange resin. This method is particularly suitable for use in isolating DCI from product mixtures produced according to the first embodiment of the present invention.

Preferably, a product mixture resulting from the acid hydrolysis of kasugamycin is dissolved in water to form an aqueous product solution. This aqueous product solution is then sequentially contacted with: (i) a basic (or anionic) ion exchange resin; and (ii) an acidic (or cationic) ion exchange resin. Preferably, the product mixture resulting from the acid hydrolysis of kasugamycin is dried in vacuo prior to being dissolved in water. According to this particularly preferred embodiment of the present invention, the acid employed in the hydrolysis of kasugamycin is preferably a volatile acid (i.e. an acid with a boiling point less than or equal to that of water) and thus may be readily removed from the product mixture by application of vacuum and/or heat. Preferably, the acid is TFA.

Following the removal of the volatile acid, the product mixture is dissolved in a suitable amount of water. Preferably, the amount of water used in the inventive method is the minimal amount necessary to dissolve the product mixture sufficiently for contacting with the ion exchange resins. Most preferably, the amount of water used is the minimal amount necessary to completely dissolve the product mixture. One skilled in the art can readily determine, through empirical means, an appropriate amount of water for a given product mixture.

The amount of basic ion-exchange resin used in the inventive method is preferably the minimal amount necessary to neutralize any residual acids in the product mixture. Such amounts may be determined empirically by one skilled in the art considering such factors as, for example, the amount of acid employed in the hydrolysis and the amount of product mixture being processed. Preferably, the amount of basic ion-exchange resin is not more than 12 times (w/w) the amount of product mixture being processed. More preferably, the amount of basic ion-exchange resin is not more than 7 times (w/w) the amount of product mixture being processed.

The amount of acidic ion-exchange resin used in the inventive method is preferably the minimal amount necessary to neutralize any residual bases in the product mixture. Such amounts may be determined empirically by one skilled in the art considering such factors as, for example, the amount of kasugamycin hydrolyzed and the amount of product mixture being processed. Preferably, the amount of acidic ion-exchange resin is not more than 6 times (w/w) the amount of product mixture being processed. More preferably, the amount of basic ion-exchange resin is not more than 4 times (w/w) the amount of product mixture being processed.

B. Derivatization

A third preferred embodiment of the present invention is directed to a method for isolating DCI from a product mixture resulting from the acid hydrolysis of kasugamycin by contacting the product mixture with a reagent that reacts with one or more of the hydroxy groups of DCI. This method is particularly suitable for use in isolating DCI from product mixtures produced according to the first embodiment of the present invention.

Preferably, a product mixture resulting from an acid hydrolysis of kasugamycin, such as the hydrolysis of kasugamycin using aqueous TFA, is dissolved or suspended in a suitable solvent to form a product solution (or suspension). The solvent may be any of the known and available solvents which will adequately dissolve or suspend the product mixture from kasugamycin hydrolysis for further processing in accordance with the methods of the present invention.

This product solution/suspension is contacted with an effective amount of a reagent that reacts with one or more of the hydroxy groups of DCI to form a DCI derivative that is more soluble in an organic solvent than in an aqueous solvent. The product solution/suspension is contacted with the reagent for a time sufficient for the desired DCI derivative to be formed.

Both an organic solvent and an aqueous solvent are then added to the product solution/suspension containing the DCI derivative to form a biphasic mixture (i.e. a mixture having an aqueous liquid phase and an organic liquid phase). While not wishing to be bound to any theory of operability, it is believed that the DCI derivative is contained in the organic liquid phase while the remaining products of the acid hydrolysis are contained in the aqueous liquid phase. Illustrative examples of suitable organic solvents include, but are not limited to, the following: ethers (e.g. methyl t-butyl ether, diethyl ether); esters (e.g. ethyl acetate), hydrocarbons (e.g. benzene); halogenated solvents (e.g. methylene chloride, chloroform); and the like.

The organic liquid phase is subsequently separated from the biphasic mixture by any of the methods and techniques known and available to those skilled in the art, such as by use of a separatory funnel. The DCI derivative is isolated from the organic liquid phase by known methods, such as the application of vacuum and/or heat. The DCI derivative may then be directly converted to DCI by any of the methods and techniques known and available to those skilled in the art, or may be further purified, for example by crystallization, prior to conversion to DCI.

The reagent that reacts with the hydroxy group(s) of DCI may be any reagent that forms a derivative of DCI that involves at least two of the hydroxy groups of DCI. Illustrative examples of suitable reagents include, but are not limited to, the following: orthoesters (including trialkylorthoformates, trialkylorthoacetaes and trialkylorthopropionates); aldehydes (e.g. propionaldehyde, butyraldehyde); ketones (e.g. acetone, butanone); dithianes; ketals (e.g. dimethoxypropane); acetals; enol ethers (e.g. 2-methoxypropene); and the like. In order to facilitate the formation of a DCI derivative, one or more suitable catalysts, preferably an acidic catalyst (e.g. hydrochloric acid, toluenesulfonic acid, an acidic ion-exchange resin, etc.), may be added during processing. Heat and/or vacuum may also be added if desired.

In one particularly preferred embodiment of the present invention, the product mixture from kasugamycin hydrolysis is dried in vacuo and then reacted with triethylorthoformate in the presence of a catalytic amount of Amberlyst® 15 acid resin to form a DCI derivative solution. Methyl t-butyl ether (an organic solvent) and alkaline water (an aqueous solvent) are added to the DCI derivative solution, the resulting organic phase is isolated and the solvent removed with vacuum and/or heat. This organic phase is then preferably treated with acid, such as hydrochloric acid, to convert the DCI derivative to DCI and the volatiles removed in vacuo to yield highly pure DCI.

In another particularly preferred embodiment, the product mixture from kasugamycin hydrolysis is dried in vacuo, suspended in DMF, and then reacted with dimethoxypropane in the presence of a catalytic amount of Amberlyst® 15 acid resin to form a DCI derivative solution. Ethyl acetate (an organic solvent) and water are added to the DCI derivative solution and the resulting organic phase is isolated. This organic phase is then preferably treated with acid, such as hydrochloric acid, to convert the DCI derivative to DCI and the volatiles removed in vacuo to yield highly pure DCI.

In still yet another particularly preferred embodiment, the product mixture from kasugamycin hydrolysis is dried in vacuo, suspended in DMF, and then reacted with 2-methoxypropene in the presence of an acid catalyst to form a DCI derivative solution. Methyl t-butyl ether and an aqueous bicarbonate solution are added to the DCI derivative solution and the resulting organic phase is isolated. This organic phase is then preferably treated with acid, such as hydrochloric acid, to convert the DCI derivative to DCI and the volatiles removed in vacuo to yield highly pure DCI.

III. Uses of DCI

The DCI produced in accordance with the present invention has a wide variety of potential uses.

For example, DCI may be used for improving glucose metabolism and/or increasing insulin sensitivity in mammals, particularly humans. These mammals may have diabetes, particularly type 2 diabetes (insulin resistant diabetes), or may have only impaired glucose tolerance or impaired fasting glucose.

In addition, DCI may be used for treating mammalian metabolic diseases characterized by abnormal glucose metabolism and/or decreased insulin sensitivity. These mammalian metabolic diseases include, but are not limited to, the following: diabetes mellitus and its chronic complications; gestational diabetes; pre-eclampsia; obesity; hyperlipidemia and/or dyslipidemia; atherosclerosis; hypertension; cardiovascular disease; AIDS; cancer; wasting and/or cachexia; sepsis; trauma, such as associated with burns, malnutrition and/or stress; aging; autoimmune diseases, such as lupus; endocrine diseases; hyperuricemia; polycystic ovary disease; and complications arising from athletic activity or inactivity.

DCI produced according to the present invention may also be administered pharmacologically as a prodrug. The expression "prodrug" as used herein denotes a derivative of DCI which is converted to DCI in vivo by an enzymatic or chemical process but exhibits enhanced delivery characteristics and/or therapeutic value. The preparation and administration of prodrugs of saccharides, for example in the form of methylated or acylated hydroxyl groups, is well known in the art. (Baker et al., *J. Med. Chem.* 27:270–274 (1984)).

Many of the organic-soluble DCI derivatives prepared according to the the present invention can serve as DCI prodrugs. For example, DCI which has been derivatized with orthoesters, ketones and/or aldehydes may be administered as a DCI prodrug in a pharmaceutical preparation. While not wishing to be bound by any theory of operability, it is believed that DCI is liberated from these DCI prodrugs by mild acid hydrolysis in vivo, as for example by hydrolysis in the presence of stomach acids.

DCI (or derivatized DCI) obtained in accordance with the present invention can also comprise the active component (or active prodrug) in a pharmaceutical composition. The pharmaceutical compositions of DCI may be administered to any animal that would benefit therefrom, particularly humans.

These pharmaceutical compositions will be formulated and dosed in a fashion consistent with good medical practice, taking into account the clinical condition of the individual patient (especially the side effects of treatment with the active agent), the site of delivery of the composition, the method of administration, the scheduling of administration, and other factors known to practitioners. The "effective amount" of each active agent (i.e. DCI or a derivative thereof) for the purposes of the present invention is determined in view of such considerations. Those skilled in the art can readily determine empirically an appropriate "effective amount" of each active agent for a particular mammalian patient.

The key factor in selecting an appropriate dose is, of course, the desired result obtained in terms of improving glucose metabolism and/or increasing sensitivity. These desired results may be measured, for example, by increases or decreases in blood glucose levels and/or insulin sensitivity in the patient. The length of treatment needed to observe changes and the interval following treatment for responses to occur may vary depending on the desired effect and the particular patient, but may be determined empirically by those skilled in the art.

As a general proposition, the total effective amount of each active agent administered per dose will be in the range of about 0.5 mg/kg/day to 1,000 mg/kg/day of mammalian patient body weight, although, as noted above, this will be subject to therapeutic discretion. More preferably, this dose is at least 0.5 mg/kg/day, and most preferably for humans between about 1 and 50 mg/kg/day.

For example, when administered orally, the composition preferably contains from about 1 mg to about 1500 mg of DCI, more preferably from about 10 mg to about 900 mg of DCI, even more preferably about 30 mg to about 600 mg of DCI.

As used herein, the phrase "pharmaceutically acceptable" is intended to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable carrier" is a pharmaceutically acceptable material, composition or vehicle, such as a liquid or solid filler, diluent, excipient, solvent or encapsulating material, involved in carrying or transporting the active agents of the inventive compositions from one organ, or portion of the body, to another organ, or portion of the body. Each carrier must be "acceptable" in the sense of being compatible with the other ingredients of the formulation and not injurious to the patient.

Some illustrative examples of materials which can serve as pharmaceutically-acceptable carriers include, but are not limited to, the following: (1) starches, such as corn starch and potato starch; (2) cellulose, and its derivatives, such as sodium carboxymethyl cellulose, ethyl cellulose and cellulose acetate; (3) powdered tragacanth; (4) malt; (5) gelatin; (6) talc; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol; (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) ethyl alcohol; (19) phosphate buffer solutions; and (20) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the inventive pharmaceutical compositions.

Illustrative examples of pharmaceutically acceptable antioxidants include, but are not limited to, the following: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredients which can be combined with a carrier material to produce a single dosage form will generally be that amount of each active ingredient which, together, produce the desired therapeutic effect. Generally, out of one hundred percent, this amount will range from about 0.01 percent to about ninety-nine percent of active ingredients, preferably from about 0.1 percent to about 90 percent, most preferably from about 1 percent to about 90 percent.

Methods of preparing these formulations or compositions include the step of bringing into association DCI (or a derivative thereof) with the carrier and, optionally, one or more accessory ingredients.

In general, the formulations are prepared by uniformly and intimately bringing into association the active ingredient with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of each active ingredient. The active ingredients of the inventive compositions may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate,potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding the active ingredient and carrier material(s), optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredients moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredients therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use.

These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredients can also be in micro-encapsulated form, if appropriate, with one or more of the above-described excipients.

Liquid dosage forms for oral administration of the inventive compositions include pharmaceutically acceptable emulsions, microemulsions, solutions, suspensions, syrups and elixirs. In addition to the active ingredients, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredients, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredients of the present invention with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active ingredients. Formulations of the present invention which are suitable for vaginal administration also include pessaries, tampons, creams, gels, pastes, foams or spray formulations containing such carriers as are known in the art to be appropriate.

Dosage forms for the topical or transdermal administration of the inventive compositions include powders, sprays, ointments, pastes, creams, lotions, gels, solutions, patches and inhalants. The active ingredient may be mixed under sterile conditions with a pharmaceutically-acceptable carrier, and with any preservatives, buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Transdermal patches have the added advantage of providing controlled delivery of a compound of the present invention to the body. Such dosage forms can be made by dissolving or dispersing the active ingredients in the proper medium. Absorption enhancers can also be used to increase the flux of the active ingredients compound across the skin. The rate of such flux can be controlled by either providing a rate controlling membrane or dispersing the active ingredients in a polymer matrix or gel. Devices, including patches, which transdermally deliver the active ingredients by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise DCI (or a derivative thereof) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Illustrative examples of suitable aqueous and nonaqueous carriers which may be employed in the pharmaceutical compositions of the invention include, but are not limited to, the following: water; ethanol; polyols, such as glycerol, propylene glycol, polyethylene glycol, and the like, and suitable mixtures thereof; vegetable oils, such as olive oil; and injectable organic esters, such as ethyl oleate. Proper fluidity can be maintained, for example, by the use of coating materials, such as lecithin, by the maintenance of the required particle size in the case of dispersions, and by the use of surfactant.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject active ingredients in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given alone or as a pharmaceutical composition containing, for example, 0.01 to 99.5% (more preferably, 0.1 to 90%) of each active ingredient together in combination with at least one pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Oral administration is particularly preferred.

The phrases "parenteral administration" and "administered parenterally" as used herein are intended to mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein are intended to mean the administration of a compound, drug or other material other than directly into the central nervous system, such that it enters the patient's system and, thus, is subject to metabolism and other like processes, for example, subcutaneous administration.

The inventive compositions may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the active ingredients of the present invention, which may be used in a suitable hydrated form, and/or the pharmaceutical compositions of the present invention, are formulated into pharmaceutically acceptable dosage forms by conventional methods known to those of skill in the art.

As noted, actual dosage levels of the active ingredient in the inventive pharmaceutical compositions may be varied so as to obtain an amount which is effective to achieve the desired therapeutic response for a particular patient, composition, and mode of administration, without being toxic to the patient.

The selected dosage level will depend upon a variety of factors, including, but not limited to, the following: the activity of DCI (or the derivative thereof); the route of administration; the time of administration; the rates of absorption, distribution, metabolism and/or excretion of the particular active ingredient being employed; the duration of the treatment; other drugs, compounds and/or materials used in combination with the particular active ingredients employed; the age, sex, weight, condition, general health and prior medical history of the patient being treated; and like factors well known in the medical arts.

A physician or veterinarian having ordinary skill in the art can readily determine the effective amount of the active ingredient required in the inventive pharmaceutical compositions. For example, the physician or veterinarian could start doses of the pharmaceutical composition at levels lower than that required in order to achieve the desired therapeutic effect and gradually increase the dosage until the desired effect is achieved.

If desired, the effective daily dose of the active ingredients may be administered as two, three, four, five, six or more sub-doses administered separately at appropriate intervals throughout the day, optionally, in unit dosage forms.

While it is possible for the active ingredients of the present invention to be administered alone, it is preferable to administer these compounds as a pharmaceutical formulation (composition).

Therapeutic compositions can be administered with medical devices known in the art. For example, a therapeutic composition of the present invention can be administered with a needleless hypodermic injection device, such as the devices disclosed in U.S. Pat. Nos. 5,399,163; 5,383,851; 5,312,335; 5,064,413; 4,941,880; 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are well known to those skilled in the art.

IV. Examples

The following examples are illustrative, but not limiting, of the present invention. Other suitable modifications and adaptations are of the variety normally encountered by those skilled in the art and are fully within the spirit and scope of the present invention.

EXAMPLES

Example 1

Hydrolysis of Kasugamycin

Kasugamycin (76% purity, 1 g), 95% trifluoroacetic acid (5 mL) and Amberlyst™ 15, $H^+$ resin (3 g) were combined and heated 4 h at 75° C., after which time silica gel TLC (solvent-butanol:acetic acid:water 2:1:1; visualization with ninhydrin) showed complete disappearance of kasugamycin. The catalyst was removed by filtration through a coarse scintered glass funnel and washed with TFA (20 mL). The solvent was removed under reduced pressure.

Variations in the amount of TFA employed affected the reaction as shown in the following table:

Effect of Varied Proporations of Trifluoracetic Acid on the Resin Hydrolysis of Kasugamycin

| Kasugamycin, g (purity) | % TFA | Amt. Resin, g | Reaction Temp. (° C.) | Reaction Time, H (% completion) |
|---|---|---|---|---|
| 1,(95%) | 98 | 3 | 76 | 4, (100%) |
| 1,(95%) | 95 | 3 | 75 | 4, (100%) |
| 10,(76%) | 90 | 3 | 85 | 4, (100%) |
| 1,(95%) | 50 | 3 | 95 | 4, (100%) |
| 1,(95%) | 10 | 3 | 90 | 4, (25%) |
| 1,(95%) | 1* | 3 | 100 | 4, (25%) |
| 1,(95%) | 95 | 0** | 80 | 24, (50%) |

*pure water
**no resin

Example 2

Ion-exchange Purification of D-Chiro-Inositol

Example 2a

Kasugamycin (10 g) hydrolyzed with 90% TFA as in Example 1 was purified with ion exchange resins using the batch method as follows. Amberlite™ IRA 410 resin (20 mL) and 20 mL deionized $H_2O$ were added to the hydrolysis mixture. After stirring for 30 minutes the resin was removed by filtration through a coarse glass scintered funnel. The resin was washed with 10 mL deionized $H_2O$ and Amberlite™ IR 120 resin (30 mL) was added to the filtrate and the mixture allowed to stir for 30 minutes. The resin was removed by filtration through a coarse glass scintered funnel and rinsed with 10 mL deionized $H_2O$. The mixture was decolorized by stirring with 0.5 g charcoal and filtered through Whatman 42 filter paper.

The resulting solution contained D-chiro-inositol at a concentration of 7.2% (w/v). Removal of the solvent in vacuo, followed by drying under reduced pressure afforded (2.87 g, 91%) of D-chiro-inositol. No impurities were detected by $^1$H-NMR. HPLC on an Econosphere Amino column (eluent-acetonitrile:water, 80:20, 1 mL/min, refractive index detection) showed a single peak.

Example 2

Kasugamycin (5 g) hydrolyzed with 95% TFA as in Example 1 was purified with ion exchange resins using the column method as follows. The hydrolysis product was dissolved in 5 mL deionized $H_2O$ and introduced into a column packed with strongly basic ion-exchange resin (Amberlite™ IRA 410, 10 mL). The eluent from this column flowed directly into a second column charged with strongly acidic ion exchange resin (Amberlite™ IR 120, 15 mL). The columns were eluted with deionized water. The eluent (20 mL) was stirred with 0.25 g charcoal and filtered through a coarse sintered glass funnel with Celite.

The resulting solution contained D-chiro-inositol at a concentration of 7.3% (w/v). Removal of the solvent in vacuo, followed by drying under reduced pressure afforded (1.46 g, 92.6%) of D-chiro-inositol. No impurities were detected by $^1$H-NMR, and HPLC showed a single peak.

Comparative Example 1

Kasugamycin hydrochloride (1 g), 5 mL deionized $H_2O$ and Diaion™ SK 116 resin (6 g) were combined and heated 4 h at 85° C., and then at 100° C. for 3 h. The catalyst was removed by filtration through a course scintered glass funnel and washed with deionized $H_2O$ (20 mL). The mixture was purified as above, using ion exchange resins and charcoal, yielding D-chiro-inositol (15%).

Comparative Example 2

Kasugamycin hydrochloride (1 g) and 2N trifluoroacetic acid (5 mL) were combined and heated 4 h at 75° C., after which time silica gel TLC (solvent-butanol:acetic acid:water, 2:1:1; Visualization with potassium permanganate stain showed kasugamycin was still present. The solution was concentrated in vacuo. The hydrolysis product was purified in the usual manner using ion exchange resins and charcoal. D-chiro-inositol was obtained in 20% yield.

Example 3

Hydrolyzed kasugamycin (1 g) was suspended in DMF (10 mL), to which was added triethylorthoformate (11 mL) and Amberlyst™ 15, $H^+$ resin (150 mg). The mixture was stirred at room temp for 16 hours, with vacuum distillation of the evolved ethanol. $NaHCO_3$ (3 g) was added and the mixture stirred for 3 hours. The mixture was filtered and partitioned between methyl t-butyl ether (30 mL) and water (20 mL). The aqueous phase was extracted with 2×20 mL MTBE and the combined organic extract dried with magnesium sulfate, filtered and evaporated to dryness.

The resulting white solid was taken into methanol:water:concentrated HCl (5:2.5:2.5) and stirred at ambient temp for 1 hours. Removal of the solvents in vacuo afforded DCI (214 mg).

Example 4

Hydrolyzed kasugamycin (1 g) was suspended in DMF (5 mL) to which was added dimethoxypropane (3.5 mL) and Amberlyst™ 15, H+ resin (150 mg). The mixture was heated at 60° C. for 16 hours, cooled and NaHCO₃ (250 mg) added. The mixture was taken into methyl t-butyl ether (20 mL), and washed with water (2×20 mL). The aqueous phase was washed with 2×10 mL MTBE and the combined organic phase was dried with magnesium sulfate, filtered and evaporated to dryness. The resulting solid was taken into methanol:water: concentrated HCl (5:2.5:2.5) and stirred at ambient temp for 1 hour. Removal of the solvents in vacuo afforded DCI (201 mg).

Example 5

Hydrolyzed kasugamycin (1 g) was suspended in DMF (5 mL) to which was added tripropyl orthoformate (5 mL) and Amberlyst™ 15, H+ resin. The mixture was stirred at room temperature for 16 hours. Sodium bicarbonate (1 g) was added and the material filtered and partitioned between methyl t-butyl ether (50 mL) and water (25 mL). The water was extracted with an additional 25 mL of MTBE. The combined organic extracts are dried, filtered and evaporated.

The resulting solid was taken into methanol-water-conc-HCl (5:2.5:2.5) and stirred at ambient temp for 1 hour. Removal of the solvents in vacuo afford DCI (169 mg).

Example 6

Hydrolyzed kasugamycin (1 g) was suspended in triethylorthoformate (15 mL). Toluenesulfonic acid (10 mg) was added and the mixture heated at 100° C. under an inert atmosphere for 16 hours. The mixture was cooled to 25° C., sodium bicarbonate (1 g) was added and the material filtered and partitioned between ethyl acetate (50 mL) and water (25 mL). The water was extracted with an additional 25 mL of ethyl acetate. The combined organic extracts were dried, filtered and evaporated.

The resulting solid was taken into methanol:water:concentrated HCl (5:2.5:2.5) and stirred at ambient temp for 1 hour. Removal of the solvents in vacuo afford DCI (246 mg).

Example 7

Hydrolyzed kasugamycin (1 g) was suspended in DMF (10 mL) to which was added methoxypropene (4.8 g) and Amberlyst™ 15, H+ resin (150 mg). The mixture was stirred at 25° C. for 2 hours. NaHCO₃ (250 mg) was added and the mixture stirred for an additional 2 hours. The mixture was filtered and the retentate washed with MTBE (5 mL). The filtrate was diluted with MTBE (20 mL), and washed with water (20 mL). The aqueous phase was washed with 2×10 mL MTBE and the combined organic phase was dried with magnesium sulfate, filtered and evaporated to dryness.

The resulting solid was taken into methanol:water:concentrated HCl (5:2.5:2.5) and stirred at ambient temp for 1 hour. Removal of the solvents in vacuo afford DCI (260 mg).

Example 8

Hydrolyzed kasugamycin (1 g) was suspended in DMF (10 mL) to which was added propionaldehyde diethylacetal (8.8 g) and Amberlyst™ 15, H+ resin (150 mg). The mixture was stirred at 25° C. for 16 hours, cooled and NaHCO₃ (2 g) added. The mixture was filtered and the retentate washed with MTBE (5 mL). The filtrate was diluted with water (50 mL). The aqueous phase was washed with 3×50 mL MTBE and the combined organic phase was dried with magnesium sulfate, filtered and evaporated to dryness.

The resulting solid was taken into methanol:water:concentrated HCl (5:2.5:2.5) and stirred at ambient temp for 1 hour. Removal of the solvents in vacuo afford DCI (236 mg).

Example 9

Hydrolyzed kasugamycin (1 g) was suspended in acetonitrile (10 mL) to which was added triethylorthoformate (9.9 g) and Amberlyst™ 15 H+ resin (150 mg). The mixture was stirred for 28 hours at 25° C. then for 6 hours at 80° C. After cooling, the mixture was treated with NaHCO₃ (2 g). The mixture was filtered and the retentate washed with ethyl acetate (5 mL). The filtrate was diluted with water (50 mL). The aqueous phase was washed with 3×50 mL ethyl acetate and the combined organic phase was dried with magnesium sulfate, filtered and evaporated to dryness.

The resulting solid was taken into methanol:water:concentrated HCl (5:2.5:2.5) and stirred at ambient temp for 1 hour. Removal of the solvents in vacuo afford DCI (210 mg).

Example 10

Hydrolyzed kasugamycin (1 g of 76% pure grade) was suspended in DMF (10 mL) to which methoxypropene (4.8 g) and Amberlyst™ 15 H+ resin (150 mg) were added. The mixture was stirred at 25° C. for 2 hours. NaHCO₃ (250 mg) was added and the mixture stirred for an additional 2 hours. The mixture was filtered and the retentate washed with t-butyl methyl ether (5 mL). The filtrate was diluted with t-butyl methyl ether (20 mL), and washed with water (20 mL). The aqueous phase was washed with 2×10 mL t-butyl methyl ether and the combined organic phase was dried with magnesium sulfate, filtered and evaporated to dryness.

The resulting solid was taken into methanol:water:concentrated HCl (5:2.5:2.5) and stirred at ambient temp for 1 hour. Removal of the solvents in vacuo yielded DCI (260 mg).

Example 11

Hydrolyzed kasugamycin (1 g of 76% pure grade) was suspended in DMF (10 ml) to which triethylorthoformate (9.88 g) and Amberlyst™ 15 H+ resin (200 mg) were added. The mixture was stirred at 25° C. for 17 hours. NaHCO₃ (2 g) was added and the mixture stirred for an additional 2 hours. The mixture was filtered and the retentate washed with ethyl acetate (10 mL). The filtrate was diluted with 10 mL ethyl acetate and washed with water (20 mL). The aqueous phase was washed with 2×20 mL ethyl acetate and the combined organic phase was dried with magnesium sulfate, filtered and evaporated to dryness.

The resulting solid was taken into methanol:water:concentrated HCl (5:2.5:2.5) and stirred at ambient temp for 1 hour. Removal of the solvents in vacuo yielded DCI (220 mg).

Having now fully described this invention, it will be understood to those of ordinary skill in the art that the methods of the present invention can be carried out with a wide and equivalent range of conditions, formulations, and other parameters without departing from the scope of the invention or any embodiments thereof. All patents and publications cited herein are hereby fully incorporated by reference in their entirety.

What is claimed is:

1. A method for producing DCI from kasugamycin, which comprises hydrolyzing kasugamycin in an aqueous solution of trifluoroacetic acid (TFA) in the presence of a strongly acidic ion exchange resin.

2. A method for isolating DCI from a product mixture resulting from the acid hydrolysis of kasugamycin by contacting the product mixture with a reagent that reacts specifically with two or more of the hydroxy groups of DCI.

* * * * *

UNITED STATES PATENT AND TRADEMARK OFFICE
CERTIFICATE OF CORRECTION

PATENT NO. : 6,342,645 B2
DATED : January 29, 2002
INVENTOR(S) : Plourde, Jr. et al.

It is certified that error appears in the above-identified patent and that said Letters Patent is hereby corrected as shown below:

<u>Title page,</u>
Item [75] Inventors, please delete "Robert Plourde, Jr., Richmond; Mark C. Sleevi, Midlothian; Rachel K. Longo, Mechanicsville, all of VA (US)" and insert therein
-- Robert Plourde, Jr., Chapel Hill, NC; Mark C. Sleevi, Midlothian; Rachel K. Longo, Mechanicsville, both of VA (US) --.

Signed and Sealed this

Twenty-first Day of May, 2002

*Attest:*

JAMES E. ROGAN
*Attesting Officer*     *Director of the United States Patent and Trademark Office*